US007610097B2

(12) United States Patent
Markoll

(10) Patent No.: US 7,610,097 B2
(45) Date of Patent: Oct. 27, 2009

(54) ELECTROMAGNETIC STIMULATION IN PATIENTS WITH OSTEOPOROSIS

(76) Inventor: Richard Markoll, Denninger Str. 104, D-81925 München (DE)

( * ) Notice: Subject to any disclaimer, the term of this patent is extended or adjusted under 35 U.S.C. 154(b) by 0 days.

(21) Appl. No.: 10/551,262

(22) PCT Filed: Apr. 7, 2004

(86) PCT No.: PCT/EP2004/003711

§ 371 (c)(1),
(2), (4) Date: Sep. 28, 2005

(87) PCT Pub. No.: WO2004/089467

PCT Pub. Date: Oct. 21, 2004

(65) Prior Publication Data

US 2006/0200214 A1 Sep. 7, 2006

(30) Foreign Application Priority Data

Apr. 10, 2003 (GB) ................................ 0308323.5

(51) Int. Cl.
*A61N 1/00* (2006.01)

(52) U.S. Cl. ................................ 607/51; 607/3; 607/50

(58) Field of Classification Search ................ 606/100, 606/1; 128/898; 607/1, 3, 50, 51, 100
See application file for complete search history.

(56) References Cited

U.S. PATENT DOCUMENTS

| | | | | |
|---|---|---|---|---|
| 4,674,482 | A * | 6/1987 | Waltonen et al. | 600/14 |
| 5,100,373 | A * | 3/1992 | Liboff et al. | 600/13 |
| 5,267,939 | A * | 12/1993 | Liboff et al. | 600/13 |
| 6,139,545 | A | 10/2000 | Utley et al. | |
| 6,443,883 | B1 * | 9/2002 | Ostrow et al. | 600/14 |
| 6,464,986 | B1 * | 10/2002 | Aoki et al. | 424/239.1 |
| 6,839,595 | B2 * | 1/2005 | Tepper et al. | 607/51 |
| 6,899,667 | B2 * | 5/2005 | Becker et al. | 600/9 |
| 2002/0032148 | A1 | 3/2002 | Uchata et al. | |
| 2002/0042633 | A1 | 4/2002 | Markoll | |
| 2002/0165583 | A1 * | 11/2002 | Tepper et al. | 607/2 |
| 2002/0176872 | A1 * | 11/2002 | Aoki et al. | 424/247.1 |
| 2003/0194427 | A1 | 10/2003 | Benja-Athon | |
| 2004/0073260 | A1 * | 4/2004 | Brighton | 607/2 |
| 2004/0077921 | A1 * | 4/2004 | Becker et al. | 600/9 |

* cited by examiner

*Primary Examiner*—Roy D. Gibson
*Assistant Examiner*—Victoria W Chen
(74) *Attorney, Agent, or Firm*—The Nath Law Group; Jerald L. Meyer; Robert T. Burns

(57) ABSTRACT

Provided is the combined use of pulsating electromagnetic signals and dose of Botulinum toxin to treat patients suffering from osteoporosis. Also provided is the use of electromagnetic signals generated by pulsating, impulse-modulated direct current for the treatment of osteoporosis.

20 Claims, 3 Drawing Sheets

Figure 1

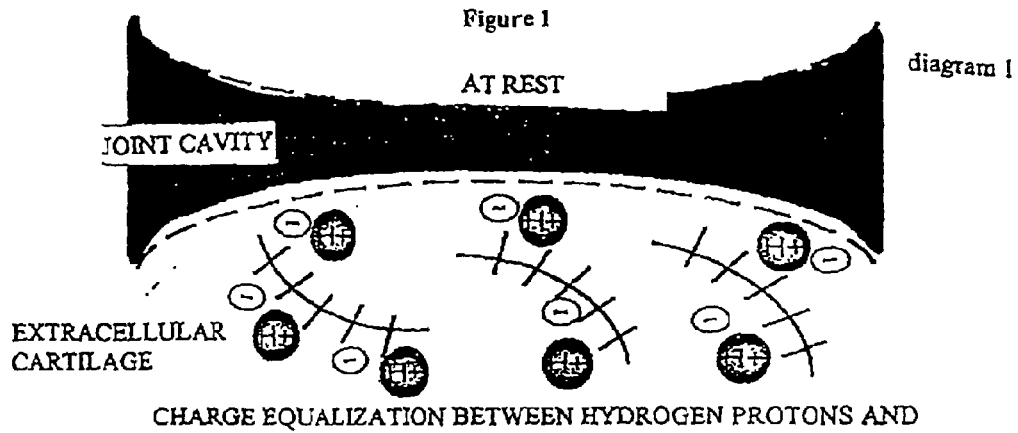

diagram 1

CHARGE EQUALIZATION BETWEEN HYDROGEN PROTONS AND NEGATIVE CHARGE CARRIERS OF THE EXTRACELLULAR CARTILAGE MATRIX –NO TENSION POTENTIAL–

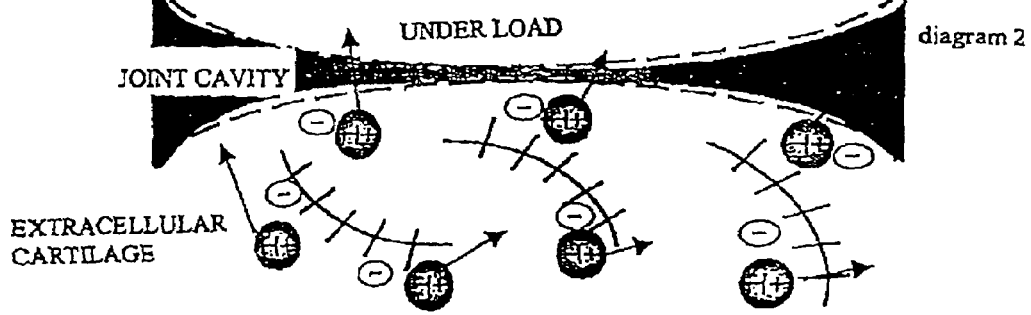

diagram 2

GENERATION OF A VOLTAGE POTENTIAL IN THE STRAINED JOINT BY "PRESSING OUT" FLUID FROM THE CARTILAGE TISSUE WITH DISPLACEMENT OF HYDROGEN PROTONS (OI I FLEXION)

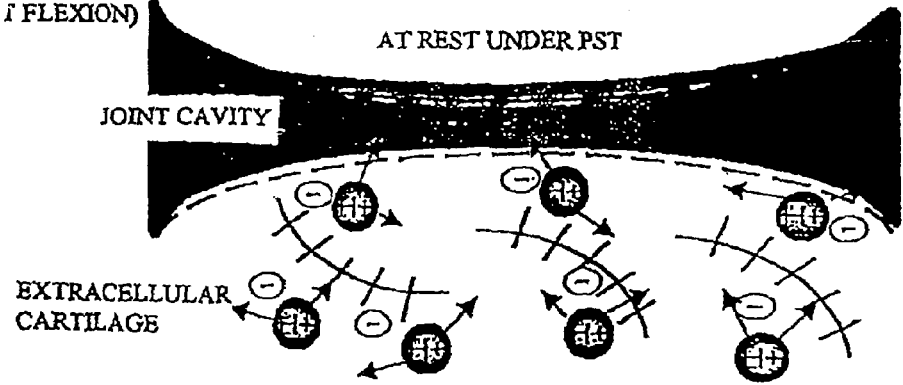

diagram 3

GENERATION OF A GREAT NUMBER OF ACTION POTENTIALS OF VARYING FLOW WITHIN THE JOINT VIA A FORCED MIGRATION OF HYDROGEN PROTONS WITHIN THE EXTRACELLULAR MATRIX BY ALTERNATING RECTANGULAR PULSE AS STIMULUS FOR THE CELLS OF THE CONNECTIVE TISSUE, PRIMARILY CHONDROCYTES.

Figure 2
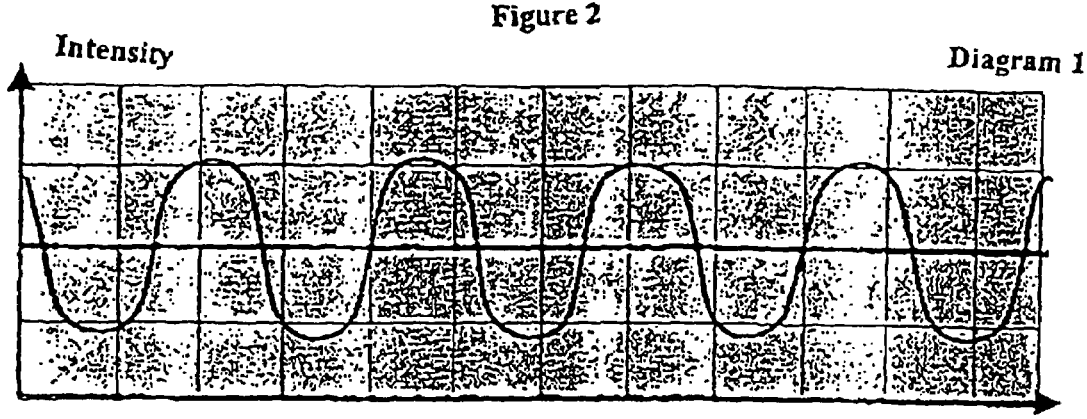
Diagram 1
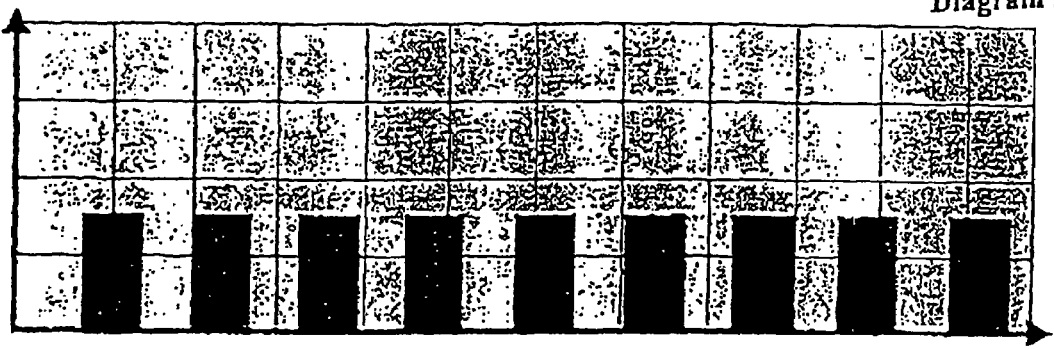
Diagram 2
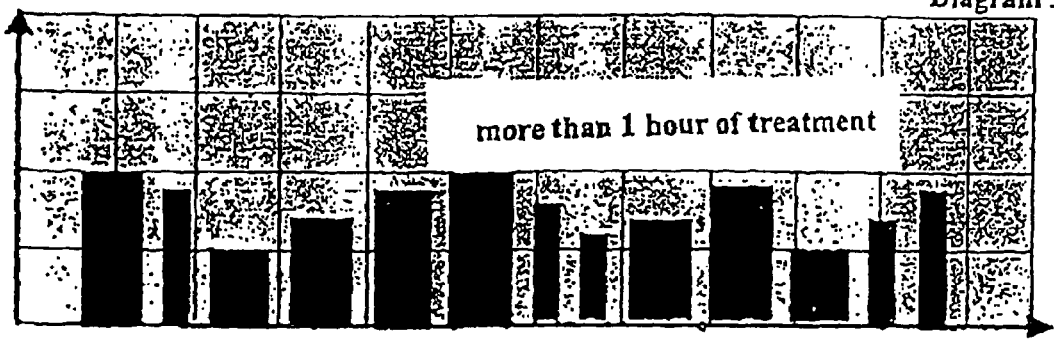
Diagram 3
more than 1 hour of treatment

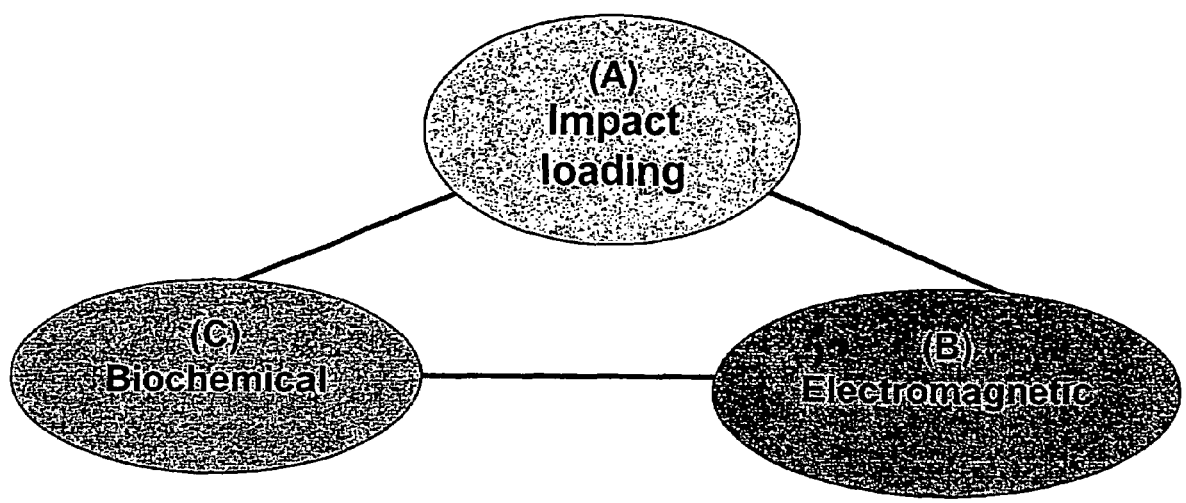

Figure 3: This figure briefly summarizes a series of events occurring at the cellular level, in response to an external/internal stimulus. In view of hard connective tissue, bone, (A) impact loading (mechanical) generates (B) a series of electric charge potentials, (biophysical; electromagnetic), subsequently modulated by surrounding connective tissue cells, to (C) activate cell signaling pathways, through various secondary messengers, gap junctions and other molecules (biochemical). One, or more pathways are subsequently activated to produce catabolic, anabolic, or other effects.

ELECTROMAGNETIC STIMULATION IN PATIENTS WITH OSTEOPOROSIS

SUMMARY OF THE INVENTION

The invention relates to the combined use of pulsating electromagnetic signals, and a specific type, and dose, of Botulinum toxin, in patients suffering from osteoporosis. Botulinum toxin was employed as an adjuvant, and found to interact synergistically with the specific pulsating electromagnetic signals, further enhancing its potential for increasing bone density.

INTRODUCTION

1. Osteoporosis—General Overview

Osteoporosis, the most common human bone disease, occurs when resorption exceeds bone formation, resulting in reduced bone mass, strength, increased bone porosity, due to deterioration, ultimately resulting in an increased risk of bone fracture.

In the United States, about 10 million individuals suffer from osteoporosis, and about 18 million more have low bone mass, placing them at increased risk for this disorder.

Osteoporosis is defined as a skeletal disorder characterized by compromised bone strength and predisposing the individual to an increased risk of fracture. Bone strength reflects the integration of two main features: bone density and bone quality. Bone density is expressed as grams of mineral per area, or volume, and in any given individual, is determined by peak bone mass and amount of bone loss. Bone quality refers to architecture, turnover, damage accumulation (for example, microfractures) and mineralization.

Osteoporosis can be further characterized as either primary or secondary. Primary osteoporosis can occur in both genders at all ages, but often follows menopause in women and occurs later in life in men. Both men and women experience an age-related decline in bone mineral density starting in midlife. Women experience more rapid bone loss in the early years following menopause, which places them at earlier risk for fractures.

In contrast, secondary osteoporosis is a result of medications, other conditions, or diseases. A large number of medical disorders are associated with osteoporosis and increased fracture risk. These can be organized into several categories: genetic disorders, hypogonadal states, endocrine disorders, gastrointestinal diseases, hematologic disorders, connective tissue disease, nutritional deficiencies, drugs, and a variety of other common, serious chronic systemic disorders, such as congestive heart failure, end-stage renal disease, and alcoholism.

Glucocorticoid use is the most common form of drug-related osteoporosis, and its long-term administration for disorders such as rheumatoid arthritis and chronic obstructive pulmonary disease, has been associated with a high fracture rate. People who have undergone organ transplant are at high risk for osteoporosis due to a variety of factors, including pre-transplant organ failure and use of glucocorticoids post-transplantation. Hyperthyroidism is a well-described risk factor for osteoporosis. In addition, some studies have suggested that women taking thyroid replacements may also be at an increased risk for excess bone loss, suggesting that careful regulation of thyroid replacement is important.

Predictors of low bone mass include female gender, increased age, estrogen deficiency, white race, low weight and body mass index (BMI), family history of osteoporosis, smoking, and a history of prior fracture. Use of alcohol and caffeine-containing beverages is inconsistently associated with decreased bone mass. In contrast, some measures of physical function and activity have been associated with increased bone mass, including grip strength and current exercise.

Onset of osteoporosis may be prevented due to the remarkable progress made in the scientific understanding of its causes, diagnosis, and treatment. Factors including, a healthy lifestyle, through diet and activity, aids in maintaining bone health, thereby decreasing the predisposition for developing osteoporosis.

2. Techniques for Diagnosing Osteoporosis

Currently there is no known available, single device, capable of accurately assessing and/or measuring overall bone strength.

The most commonly used measurement to diagnose osteoporosis and predict fracture risk, is based on assessment of bone mineral density (BMD), principally determined by assessing bone mineral content. BMD accounts for approximately 70 percent of bone strength.

BMD measurements have been shown to correlate strongly with the load-bearing capacity of the hip and spine, as well as, fracture risk. Several different techniques have been developed to assess BMD at multiple skeletal sites, including the peripheral skeleton, hip, and spine.

The World Health Organization (WHO) has selected BMD measurements to establish criteria for the diagnosis of osteoporosis. A T-score is defined as the number of standard deviations (SD) above or below the average BMD value for young healthy white women. This should be distinguished from a Z-score, which is defined as the number of SD above or below the average BMD for age- and gender-matched controls.

According to the WHO definition, osteoporosis is present when the T-score is at least minus 2.5 SD below the mean for young white adult women. Although T-scores were originally based on the assessment of BMD at the hip, by dual-energy X-ray absorptiometry (DEXA; DXA), they have been extended to define diagnostic thresholds at other skeletal sites, and also for other technologies.

Newer measures of bone strength, such as ultrasound, have been introduced. Recent prospective studies using quantitative ultrasound (QUS) of the heel have predicted hip fracture and all non-vertebral fractures, nearly as well as DEXA, at the femoral neck.

QUS and DEXA at the femoral neck provide independent information about fracture risk, and both of these tests predict hip fracture risk better than DEXA at tlumbar spine. In general, clinical trials of pharmacologic therapies have utilized DEXA, rather than QUS, for entry criterion for studies, and there is uncertainty regarding whether the results of these trials can be generalized to patients identified by QUS as predisposed to have a high fracture risk.

In addition to effects on bone mass, bone micro-architecture, and macro-geometry, bone strength is also affected by the rate of bone remodeling. Bone remodeling can be assessed by the measurement of surrogate markers of bone turnover in the blood or urine.

These markers include bone-specific alkaline phosphatase and osteocalcin, which are indices of bone formation, and, the urinary levels of pyridinolines and deoxypyridinolines and serum and urine levels of type I collagen telopeptides (CTX and NTX), which are indices of bone resorption. The level of these markers may identify changes in bone remodeling within a relatively short time interval (several days to months), before changes in BMD can be detected. However, according to available data, marker levels do not predict bone mass or fracture risk and are only weakly associated with changes, in bone mass. Therefore, they are of limited utility in the clinical evaluation of individual patients.

3. Conventional Medications for Osteoporosis

In the past 30 years, major strides have been made in the treatment of osteoporosis.

There is consensus that adequate vitamin D and calcium intake is required for bone health. Calcium and vitamin Dmodulate age-related increases in parathyroid hormone (PTH) levels and bone resorption. Clinical trials have demonstrated that adequate calcium intake from diet or supplements, increases spine BMD and reduces vertebral and non-vertebral fractures. Low levels of 25-OH vitamin D are common in the aging population, and significant reductions in hip, and other non-vertebral, fractures have been observed in patients receiving calcium and vitamin D3 in prospective trials. The maximal effective dose of vitamin D is uncertain, but thought to be 400 to 1,000 IU/day.

Bisphosphonates, including cyclic etidronate, alendronate, and risedronate, prevent bone loss and increase BMD at the spine and hip, in a dose-dependent manner. Furthermore, they appear to reduce the risk of vertebral fractures by 30 to 50 percent. Alendronate and risedronate reduce the risk of subsequent non-vertebral fractures in women with osteoporosis and adults with glucocorticoid-induced osteoporosis. There is uncertainty about the effect of anti-resorptive therapy in reducing non-vertebral fractures in women, without osteoporosis. Side effects are generally mild. However, potential side effects include GIT and irritation of the esophagus.

The development of selective estrogen receptor modulators (SERMs) has been an important new thrust in osteoporosis research. The mechanism of action of these agents is to maximize the beneficial effects of estrogen on bone, and to minimize or antagonize the deleterious effects on the breast and endometrium. Raloxifene, a SERM approved by the FDA for the treatment and prevention of osteoporosis, has been shown to reduce the risks of vertebral fracture by 36 percent in large clinical trials. However, there is a small risk of deep venous thrombosis.

Hormone replacement therapy (HRT) is an established approach for osteoporosis treatment and prevention. Many short-term studies, and some long-term studies, with BMD as the primary outcome, have shown significant efficacy.

There is a great deal of public interest in natural estrogens, particularly plant-derived phytoestrogens. These compounds have weak estrogen-like effects, and although some animal studies are promising, no effects on fracture reduction in humans have been shown. No increase in the risk of breast cancer has been observed for up to 5 years of HRT with, for example, estrogens. However, there may be a small increased risk after 5 years, and in addition, there may be an increased risk of thromboembolism.

Salmon calcitonin has demonstrated positive effects on BMD at the lumbar spine, but this effect is less clear at the hip. Other than a recently completed randomized controlled trial of nasal calcitonin, no analysis of fracture risk is available. The main side effects are nasal irritation, from the spray form, and nausea, from the injectable form.

DESCRIPTION OF THE ILLUSTRATIONS

FIG. 1:

Diagram 1:Charge equalization between hydrogen protons and carriers of negative charges in the extracellular cartilage matrix.

Diagram 2:Generation of a voltage potential in the strained joint by pressing out fluid from the cartilage tissue with displacement of hydrogen protons.

Diagram 3: Generation of a great number of action potentials of varying flow within the joint, via a forced migration of hydrogen protons within the extracellular matrix, by alternating rectangular pulses as stimulus for the cells of the connective tissue, primarily chondrocytes.

FIG. 2:

Diagram 1:Diagram of a Krause-Lechner spool working with alternating current magnetic fields generating a sinusoidal curve. This is a non-physiological form of energy transfer.

Diagram 2:Diagram showing the application of pulsating, electromagnetic fields. A direct-current signal is applied that is continuously repeated. It is transmitted at a particular intensity and at a particular frequency. This pulse remains constant for the duration of joint treatment.

Diagram 3:Diagram with alternating rectangular pulses as stimulus, transmitted in alternating directions for the duration of treatment. The intensity of the rectangular pulses ranges mostly from 0.5 to 1.5 milliTesla. The frequency lies within the range of 1 to 30 Hertz. This type of stimulation is of relatively low frequency and energy, with respect to field strength.

FIG. 3: This figure briefly summarizes a series of events occurring at the cellular level, in response to an external/internal stimulus. In view of hard connective tissue, bone, (A) impact loading (mechanical) generates (B) a series of electric charge potentials, (biophysical; electromagnetic), subsequently modulated by surrounding connective tissue cells, to (C) activate cell signaling pathways, through various secondary messengers, gap junctions and other molecules (biochemical). One, or more pathways are subsequently activated to produce catabolic, anabolic, or other effects.

DETAILED DESCRIPTION OF THE INVENTION

The object of the invention is to increase bone density in patients suffering from osteoporosis.

According to the invention, the above object is solved by the subject matter of the claims.

It was found that by using a specific constellation of electromagnetic signals generated by pulsing, pulse-modulated, quasi-rectangular, unidirectional, direct current, bone density could be increased. The signaling device delivering these signals as therapy, is known as Pulsed Signal Therapy (PST®).

The earlier so-called magnetic field therapy, as for example, Krause-type, is defined as a sinusoidal, continuous alternating current, applied with a frequency of 44 to 77 Hz, and field strength, of approximately 2 G.

In contrast, the frequency used in this invention is in the range 1 to 30 Hz, preferably 5 to 15 Hz, with field strength in the range 1 to 20 G, preferably 10 to 15 G, but most preferably 12.5 G.

It is particularly advantageous for the modulation to be quasi-rectangular. The electromagnetic signals used according to the invention are pulsating signals. As a result, weak electromagnetic fields are transmitted to the body.

The present invention is based on several previous clinical studies that used the device to generate pulsed magnetic fields, as described above. In these studies, PST® demonstrated efficacy and safety, with no reported adverse effects, in the treatment of osteoarthritis (OA or Arthrosis), and joint-associated soft tissue injury (traumatic, including soft tissue injury). It resulted in restoration of the natural physiologic stimulus, necessary for cartilage production and treatment of connective tissue lesions, thereby ensuring continued activities of daily living and pain relief, amongst others. Moreover, it showed success in the treatment of tinnitus and temporomandibular joint disorder (TMJ).

Electromagnetic signals generated by pulsing, pulse-modulated, quasi-rectangular, unidirectional, direct current have not been previously used in patients for the treatment of osteoporosis.

According to the invention pulsed signal therapy (PST®) is being applied for the first time to increase bone density in patients with proven osteopeny or onset osteoporosis and was found to be effective.

In particular, the pulsed signal therapy (PST®) is used together with Botulinum toxin, which is used as an adjuvant. An adjuvant is an agent administered either alone, or simultaneously with, or in combination with, the main therapy, to achieve some desired effect. Here the main therapy is PST®.

This led to a an increase in bone density. It was found that Botulinum toxin, employed as an adjuvant, synergistically interacted with PST® specific, pulsating electromagnetic signals, to further enhance its bone density, stimulating potential.

Botulinum toxin is a bacterial neurotoxin that has shown its mettle as a therapeutic agent. There are eight serotypes (A, B, C1, C2 and D-G), of which type A is the most potent and the one most commonly used in clinical practice.

It is employed as a research tool in studies aimed at elucidating the mechanisms involved in vesicle trafficking and in gaining an understanding of the underlying events of synaptic transmission (www.listslabs.com).

Clinically, it is used to treat certain neuromuscular disorders in humans as well as in rejuvenation treatments and as classical anaesthetics [Turton K; Chaddock J A, Acharya K R. (2002). Botulinum and tetanus neurotoxins: Structure, function and therapeutic utility. *TRENDS in Biochemical Science,* 27(11) 552-558; Matarasso A, Deva A K, American Society of Plastic Surgeons DATA Committee. (2002). Botulinum Toxin. Safety and Efficacy Report. *Plastic and Reconstructive Surgery,* 109(3) 1191-1197]

Other applications include its use in combination with surgical and non-surgical techniques for facial rejuvenation, reduction of wrinkles and frown lines, soft tissue augmentation, facial and nerve disorders, including chronic tension-type or migraine headaches.

In Multiple Sclerosis, a disorder characterized by axonal damage, demyelination and subsequent lack of efficient neuronal transmission, this toxin has shown to have therapeutic benefits.

There are two types of Botulinum toxin, namely type A and B. While there is only one form of Type B, commercially available and marketed as Myobloc™, Type A is composed of two forms, namely Botox® and Dysport®. Of Type A and B, Type A is the most commonly used, with Botox® the preferred form, mainly due to the fact that 2.5 to 5 times less dose is required, to achieve the same effect.

In general, the effects of Botulinum toxin are dose-dependent. Therefore, the type of medical condition being treated must be considered. In addition to the medical condition, the site of administration (muscle) must be considered, such that a minimal volume of toxin is used to achieve a desired, maximum effect. The lethal dose, causing 50 percent of deaths in humans (LD50), for a 70-kg adult male, has been found to be 2500 to 3000 U (35-40 U/kg) for Botox® (Matarasso et al), and 144000 U for Myobloc™ (Matarasso et al).

Botox® is supplied as a freeze-dried vial, containing 100 units (U), to be diluted with preservative-free normal saline (1 ml-3 ml), and should ideally be used within 4 hours of reconstitution [http://www.emedicine.com/pmr/topic216.htm Botulinum Toxin: Overview and Matarasso et al].

The dosing range used is 20 U to 600 U, with the preferred range 50 U to 300 U. The volume injected is in the range 1 ml to 5 ml, with the preferred range being 0.5 ml to 1.0 ml.

In situations where the patient is immune to the effects of Botox®, Botulinum toxin type B, Myobloc™ is used. It is available as a ready-to-use solution, in 3 vial sizes (that is, 2500 U, 5000 U, and 10000 U), such that reconstitution is not warranted. It is stable for up to 21 months stored in the refrigerator. Dosing is in the range 1 U to 20000 U, and volume injected, in the range 0.05 ml to 5 ml.

According to the invention, Botulinum toxin is administered intramuscularly, intravenously, or subcutaneously, in combination with the pulsating signals.

The selection criteria for this study was based on clinical experience of the impacts and adverse effects caused by proven osteopeny or the onset of osteoporosis.

The effect on both the trabecular and cortical layers, of bone, was evaluated.

Postmenopausal women, not taking drugs affecting the skeletal system, with the exception of calcium (1,000 mg) and vitamin D3 (800-1,000 IU), and diagnosed with either trabecular osteopeny or onsettrabecular osteoporosis (without fractures), using a validated instrument of measurement, and complying with the selection criteria, were chosen. Both trabecular and cortical bone densities were measured in the non-dominant, ultra-distal radius, not supporting body weight. The bilaterally symmetrical, non-treated radius, was used as the control.

Following the treatment period, measurements were performed at 3, 6 and 12 months (the latter being the end-point of treatment). A significant loss of minerals, in any of the patients, after 3 or 6 months, immediately resulted in their withdrawal from the study. These were then placed on anti-osteoporosis continuation therapy. Patients with advanced osteoporosis, or a history of fractures, as a cause of osteoporosis, were excluded from the study.

Investigations carried out in this study, sought to elucidate whether PST® had a general, positive effect on bone density, throughout the body. This could be attributed either as an increase in mineral content, or prevention of loss thereof—mineral loss being a feature of postmenopausal osteoporosis, with an increased turnover rate, especially of trabecular bone, and concomitant increase in bone loss. Furthermore, in addition to assessing the time period, from the end of treatment, to the time when these positive effects were first observed, the long-term efficacy of the treatment regime was also evaluated. Another particular dimension investigated, was the local and/or systemic effects of the treatment (invention). That is to say, were the positive effects observed confined to the area receiving the treatment directly (local effect), or were these effects evident throughout the body (systemic effect).

Since the body is bilaterally symmetrical, positive effects, namely an increase in bone density, observed upon measuring the related radius, not subjected to treatment, implied a systemic effect.

According to the invention, electromagnetic pulses with three fixed amplitudes and frequencies are employed. Frequency, amplitude and duration of treatment are program-controlled by a processor.

Various combinations of frequency and amplitude were used for the treatment, and controlled automatically by the program. The frequencies lie within the range 1 and 30 Hz, with field strengths, within 1 and 20 G.

One-hour daily treatments, were conducted over twelve consecutive days. No examinations were performed during the treatment period During administration of treatment, the patient was seated comfortably, and the wrist positioned correctly in the device. The device was switched on, and the patient asked to sit immobile during the 1-hour treatment period. Follow-up examinations were performed at:

three months post-treatment
six months post-treatment
twelve months post-treatment Following each examination, both trabecular and cortical bone densities (volumetric BMD, vBMD) were measured in the non-dominant ultra-distal radius, not supporting body weight. The bilaterally symmetrical, non-treated radius, of each patient, was used as the control.

Bone density measurements were performed using high-resolution, magnetic peripheral quantitative computed tomography (Densiscan 1000, Scanco Medical AG, Zurich). This device enables detailed analysis of bone microarchitecture at a high resolution of 0.2 mm (lateral, cut width 1 mm) and allows the high-precision selective, volumetric determination of trabecular and cortical bone densities (Ruegsegger et al. 1990, 1994, 1996, Neff et al. 1995). Due to the long-term reproducibility of ±0.15% in the phantom, ±0.3% in mixed groups and ±~0.2 to ±0.4% in osteoporosis, it is possible to accurately determine the loss in bone mass and, in particular, to differentiate between fast losers and slow losers, in a second measurement, at three to six months post-treatment, depending on the initial bone mass.

In the resting state, and absence of mechanical loading, the use of this invention and its signal, energy parameters, cause a multitude of differentially flowing energy potentials in the joint. This is achieved by continuously changing ion-flow patterns, of quasi-rectangular pulses, forcing hydrogen protons to migrate within the extracellular matrix of the joint. As a result, a multitude of multidirectional potentials are generated leading to an increase in hard connective tissue cell activity.

Following the above study protocol using PST® alone for the treatment of osteoporosis, a 7 to 8 percent increase in bone mineral density (BMD) was demonstrated within 3 to 6 months. In contrast, documented studies, using conventional drugs used to treat osteoporosis, demonstrated a 5 to 7 percent increase, on average, after 36 months (Orwoll E et al Alendronate for the treatment of osteoporosis in men. *N Engl J Med* 2000 Aug. 31; 343(9):604-10, Orwoll E S et al. The effect of teriparatide [human parathyroid hormone (1-34)] therapy on bone density in men with osteoporosis. *J Bone Miner Res* 2003 January; 18(1): 9-17, Zanchetta J R et al. Effects of teriparatide [recombinant human parathyroid hormone (1-34)] on cortical bone in postmenopausal women with osteoporosis. *J Bone Miner Res* 2003 March; 18(3): 539-43).

In the current study, some patients undergoing PST® treatment, demonstrated an overall average BMD increase between 25 and 37 percent. Further careful analysis of the study data, led to the observation that, in this subgroup, each patient had some concomitant medical condition (for example, a rheumatic disease, or common flu, inter alia), that essentially resulted in an increased immune response. These medical conditions were varied, but were all associated with an increased immune response and all demonstrated significant increases in bone density.

Botulinum toxin, well exploited for its use in laboratory research and diverse medical applications, as already discussed, was chosen and employed as adjuvant. With the intention of creating a similar situation, it was found that by using Botulinum toxin as an adjuvant, such a non-specific, immune response, could be induced in patients with osteoporosis.

Thus the combination of PST® and the administration of Botulinum toxin, ensures maximum therapeutic benefit, that is, an increase in BMD and a subsequent decrease in fracture risk.

The invention claimed is:

1. Method for treating osteoporosis in a patient, comprising:

exposing the patient to electromagnetic signals generated by pulsating, impulse-modulated direct current, having a frequency of 1 to 30 Hz and a field strength of 1 to 20 G; and administering Botulinum toxin to the patient, wherein the Botulinum toxin synergistically interacts with the electromagnetic signals, by inducing a non-specific immune response to further enhance a bone density stimulation from the exposure of the patient to the electromagnetic signals.

2. Method according to claim 1, characterised in that the modulation form is quasi-rectangular.

3. Method according to claim 1, characterised in that the frequency is approximately 5 to 15 Hz.

4. Method according to claim 1, characterised in that the field strength is approximately 10 to 15 G.

5. Method according to claim 4, characterised in that the preferred field strength is approximately 12.5 G.

6. Method according to claim 1, characterised in that the pulses are modulated.

7. Method for administering a treatment to a patient including administration of a neurotoxin, the method comprising:

providing a pharmaceutical composition comprising Botulinum toxin;

administering the Botulinum toxin to the patient intramuscularly, intravenously, or subcutaneously; and exposing the patient to electromagnetic signals generated by pulsating, pulse-modulated, unidirectional, direct current, with frequency between 1 and 30 Hz and field strength, 1 to 20 G, wherein the Botulinum toxin synergistically interacts with the electromagnetic signals, by inducing a non-specific immune response to further enhance a bone density stimulation from the exposure of the patient to the electromagnetic signals.

8. Method according to claim 7, characterised in that the modulation form is quasi-rectangular.

9. Method according to claim 7, characterised in that the frequency is approximately 5 to 15 Hz.

10. Method according to claim 7, characterised in that the field strength is approximately 10 to 15 G.

11. Method according to claim 10, characterised in that the field strength is approximately 12.5 G.

12. Method according to claim 7, characterised in that the pulses are modulated.

13. Method according to claim 7, characterised by using a dose of Botulinum toxin Type A in the range of 20 U to 600 U, applied as a neurotoxin adjuvant to said exposing the patient to electromagnetic signals.

14. Method according to claim 7, characterised by using Botulinum toxin Type A in the range of 50 U to 300 U, applied as a neurotoxin adjuvant to said exposing the patient to electromagnetic signals.

15. Method according to claim 7, characterised by using Botulinum toxin Type B in the range 1 U to 2000 U, applied as a neurotoxin adjuvant to said exposing the patient to electromagnetic signals.

16. Method according to claim 1, characterised by using a dose of Botulinum toxin Type A in the range of 20 U to 600 U, applied as a neurotoxin adjuvant to said exposing the patient to electromagnetic signals.

17. Method according to claim 1, characterised by using a dose of Botulinum toxin Type A in the range of 50 U to 300 U, applied as a neurotoxin adjuvant to said exposing the patient to electromagnetic signals.

18. Method according to claim 1, characterised by using a dose of Botulinum toxin Type B in the range 1 U to 2000 U, applied as a neurotoxin adjuvant to said exposing the patient to electromagnetic signals.

19. Method according to claim 1, wherein a combination of exposing the patient to electromagnetic signals generated by pulsating, pulse-modulated, unidirectional direct current using Pulsed Signal Therapy (PST®) and administering Botulinum toxin enhances therapeutic benefit, including increase in bone mineral density (BMD) and a subsequent decrease in fracture risk.

20. Method according to claim 7, wherein a combination of exposing the patient to electromagnetic signals generated by pulsating, pulse-modulated, unidirectional direct current using Pulsed Signal Therapy (PST®) and administering Botulinum toxin enhances therapeutic benefit, including increase in bone mineral density (BMD) and a subsequent decrease in fracture risk.

* * * * *